United States Patent
Ng

(10) Patent No.: US 8,800,353 B2
(45) Date of Patent: Aug. 12, 2014

(54) HUMIDITY AND OSMOTIC SUCTION-CONTROLLED BOX

(75) Inventor: Charles Wang Wai Ng, Hong Kong (CN)

(73) Assignee: The Hong Kong University of Science and Technology, Kowloon (HK)

( * ) Notice: Subject to any disclaimer, the term of this patent is extended or adjusted under 35 U.S.C. 154(b) by 313 days.

(21) Appl. No.: 13/229,358

(22) Filed: Sep. 9, 2011

(65) Prior Publication Data

US 2012/0060588 A1 Mar. 15, 2012

Related U.S. Application Data

(60) Provisional application No. 61/381,645, filed on Sep. 10, 2010.

(51) Int. Cl.
*G01N 13/04* (2006.01)
*G01N 33/24* (2006.01)

(52) U.S. Cl.
CPC ........ *G01N 13/04* (2013.01); *G01N 2203/0025* (2013.01); *G01N 33/24* (2013.01)
USPC ..................... 73/73; 73/74; 73/865.6; 73/866

(58) Field of Classification Search
USPC .............................. 73/73, 74, 76, 865.68, 866
See application file for complete search history.

(56) References Cited

U.S. PATENT DOCUMENTS

| | | | | |
|---|---|---|---|---|
| 2,534,718 A * | 12/1950 | Leas et al. | ......................... | 73/38 |
| 4,561,293 A * | 12/1985 | Richards | ............................ | 73/73 |
| 4,715,212 A * | 12/1987 | Johanson | ........................... | 73/38 |
| 4,734,649 A * | 3/1988 | Barnaby | ........................ | 324/376 |
| 5,161,407 A * | 11/1992 | Ankeny et al. | .................... | 73/38 |
| 5,226,310 A * | 7/1993 | Steiger | .............................. | 73/38 |
| 5,275,063 A * | 1/1994 | Steiger et al. | ................ | 73/865.6 |
| 5,969,242 A * | 10/1999 | Hubbell et al. | ............. | 73/152.51 |
| 6,055,850 A * | 5/2000 | Turner et al. | ...................... | 73/38 |
| 6,234,008 B1 * | 5/2001 | Sjoblom et al. | .................... | 73/73 |
| 6,289,725 B1 * | 9/2001 | Hubbell et al. | .................... | 73/73 |
| 6,718,835 B2 | 4/2004 | Wang et al. | | |
| 6,719,488 B2 * | 4/2004 | Kuroda et al. | .................. | 405/36 |
| 7,143,653 B2 * | 12/2006 | Abdel-Hadi et al. | ........... | 73/819 |
| 7,222,519 B2 * | 5/2007 | Ekanayake | ........................ | 73/73 |
| 7,793,552 B2 | 9/2010 | Ng | | |
| 2007/0082600 A1 * | 4/2007 | Asvestas et al. | .............. | 454/191 |
| 2009/0049924 A1 * | 2/2009 | Ng | .................................. | 73/818 |

OTHER PUBLICATIONS

Ng, et al. "Advanced Unsaturated Soil Mechanics and Engineering". Taylor & Francis, London and New York, 2007. 710 pages.

(Continued)

*Primary Examiner* — David A Rogers
(74) *Attorney, Agent, or Firm* — Amin, Turocy & Watson, LLP

(57) ABSTRACT

Described herein are systems, apparatuses and methods for the design and use of a suction-controlled box for the measurement of stress-dependent soil and water characteristics, shear strength, volume changes and consolidation characteristics from a single unsaturated soil specimen. The suction-controlled box can include a suction control part and a mechanical loading part, which can apply various suctions and mechanical loadings to test a specimen for a full range of suctions. The suction-controlled box can also include a helical water compartment that can flush diffused air bubbles.

20 Claims, 9 Drawing Sheets

(56) References Cited

OTHER PUBLICATIONS

Pierre Delage, et al., "An evaluation of the osmotic method of controlling suction.", 24 pages.

J. Krahn, et al., "On total matric and osmotic suction", Soil Science, vol. 114, No. 5, pp. 339-348, 1972.

Anh-Minh Tang, et al., "Controlling suction by the vapour equilibrium technique at different temperatures and its application in determining the water retention properties of MX80 clay." Can. Geotech. J. 42: 287-296 (2005).

Ghao, "The Development of a New Automatic Control Apparatus for Measuring Air-Water Movements and Permeability in Unsaturated Soil", 2006, Xi'an University of Technology Senior Thesis (Abstract Translated from Chinese).

Hilf, (1956): "An investigation of pore water pressure in compacted cohesive soils", Technical Memo 654, Denver, Bureau of Reclamation.

Delage et al. (1998): "The relationship between suction and swelling properties in a heavily compacted unsaturated clay", Engineering Geology, 50, 31-48.

Ng et al. 2007. "Advanced Unsaturated Soil Mechanics and Engineering". London: Taylor & Francis, ISBN 978-0-415-43679-3., pp. 36-61.

Ng et al. (2007). "The axis-translation and osmotic techniques in shear testing of unsaturated soils: a comparison". Soils and Foundations, vol. 47, No. 4, 675-684.

\* cited by examiner

US 8,800,353 B2

HUMIDITY AND OSMOTIC SUCTION-CONTROLLED BOX

RELATED APPLICATION

This patent application claims priority to U.S. Provisional Patent Appln. No. 61/381,645, entitled "Humidity and Osmotic Suction-Controlled Box," filed Sep. 10, 2010, the entirety of which is incorporated herein by reference.

TECHNICAL FIELD

This disclosure relates generally to measurement of mechanical and hydraulic properties of saturated and unsaturated soils, and in particular to the design and use of a suction-controlled box to facilitate these measurements.

BACKGROUND

Accurate testing and measurement of mechanical and hydraulic properties of saturated and unsaturated soils is vital for various projects. These projects can include various geotechnical and geoenvironmental engineering projects, such as evaluating a stability of natural slopes, designing a pavement or a foundation needed, determining a behavior of earth structures, investigating the effectiveness of landfill covers and creating new land through land reclamation. These projects require an accurate testing and measurement of four vital soil properties: shear strength, stress-dependent soil-water characteristic curve (illustrating the water retention capability of an unsaturated soil at a given suction), consolidation, and volume change (e.g., swelling and shrinkage).

No testing apparatus exists that can test the four vital soil properties in a single sample at suctions ranging from 0 to 1,000 MPa. Instead, separate testing apparatuses exist that all require a different soil specimen. Accordingly, to obtain the required four vital soil properties, four different soil specimens must be tested. Due to natural variability and sample disturbance in different soil specimens, using four different soil samples is not reliable, and consistent results and parameters cannot be achieved. Additionally, the process of using four different samples and four test procedures is time consuming and uneconomical.

The above-described deficiencies of conventional sensing devices are merely intended to provide an overview of some of problems of current technology, and are not intended to be exhaustive. Other problems with the state of the art and corresponding benefits of some of the various non-limiting embodiments described herein may become further apparent upon review of the following detailed description.

SUMMARY

The following presents a simplified summary to provide a basic understanding of some aspects described herein. This summary is not an extensive overview of the disclosed subject matter. It is not intended to identify key or critical elements of the disclosed subject matter, or delineate the scope of the subject disclosure. Its sole purpose is to present some concepts of the disclosed subject matter in a simplified form as a prelude to the more detailed description presented later.

To correct for the above noted deficiencies and other drawbacks of current soil testing apparatuses, an apparatus that can provide an integrated testing platform for four vital soil properties, including shear strength, stress-dependent soil-water characteristic curve, consolidation, and volume change (e.g., swelling and shrinkage), in a single sample for a full range of suctions (e.g. 0-1,000 MPa) is provided.

In an embodiment, a suction-controlled box is provided. The suction-control box can provide an integrated testing apparatus for four vital soil properties, including shear strength, stress-dependent soil-water characteristic curve, consolidation, and volume change (e.g., swelling and shrinkage), and other hydraulic soil properties, in a single sample. The suction control box can include a suction control part and a mechanical load part. The suction control part can employ different components that can enable the suction-control box to be operational at all suctions (e.g., 0-1,000 MPa). The different components can include an axis translation component for low suctions (0-about 500 kPa), an osmotic control component for medium suctions (about 500 kPa-about 10 MPa) and a humidity control component for high suctions (greater than about 10 MPa). The mechanical load part can employ a horizontal loading component and a vertical loading component to test various mechanical properties. This can allow various mechanic loadings and suctions to be applied to test a single soil specimen.

In another embodiment, a suction-control box is provided. The suction-control box can provide an integrated testing apparatus for four vital soil properties, including shear strength, stress-dependent soil-water characteristic curve, consolidation, and volume change (e.g., swelling and shrinkage), and other hydraulic or mechanical soil properties, in a single sample. The suction-control box can include a suction control part and a mechanical load part as described above. The suction-control box can also include a helical water compartment or pedestal. The helical water compartment can flush diffused air bubbles out of the suction-control box. This can facilitate more accurate test results for various mechanical loadings and suctions that can be applied to test a single soil specimen without extraneous air bubbles.

According to a further embodiment, methods are provided that can facilitate testing various soil properties using a single sample for a range of suctions (e.g., 0-1,000 MPa). For example, the apparatuses described herein can perform the method described herein. However, it is conceived that other apparatuses can be adapted to perform the method.

The following description and the annexed drawings set forth in detail certain illustrative aspects of the disclosed subject matter. These aspects are indicative, however, of but a few of the various ways in which the principles of the innovation may be employed. The disclosed subject matter is intended to include all such aspects and their equivalents. Other advantages and distinctive features of the disclosed subject matter will become apparent from the following detailed description of the innovation when considered in conjunction with the drawings.

BRIEF DESCRIPTION OF THE DRAWINGS

Non-limiting and non-exhaustive embodiments of the subject disclosure are described with reference to the following figures, wherein like reference numerals refer to like parts throughout the various views unless otherwise specified.

DETAILED DESCRIPTION

In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Described herein are various embodiments of a suction-controlled box applicable in the field of geotechnical and geo-environmental engineering. The various embodiments of the suction-controlled box can include an integrated Humidity and Osmotic Suction-Controlled Box (or HosmoBox). The various embodiments of the suction-controlled box can test and/or measure various mechanical and hydraulic properties of saturated or unsaturated soil, including shear strength, stress-dependant soil-watch characteristic curve (SDSWCC) and indirect permeability functions, consolidation behavior (including settlement), volume (including swelling and shrinkage), water content, and the like. The various embodiments of the suction-controlled box can provide a single integrated system that can test these mechanical and hydraulic behaviors and properties from a single unsaturated soil specimen. Also, the various embodiments of the suction-controlled box can control a full range of suction suctions (e.g., from 0 to 1,000 MPa).

Reference throughout this specification to "various embodiments," "one embodiment," or "an embodiment," means that a particular feature, structure, or characteristic described in connection with the embodiment is included in at least one embodiment. Thus, the appearances of the phrase "in one embodiment," or "in an embodiment," in various places throughout this specification are not necessarily all referring to the same embodiment. Furthermore, the particular features, structures, or characteristics may be combined in any suitable manner in one or more embodiments.

The words "exemplary" and "example" is used herein to mean serving as an example, instance, or illustration. For the avoidance of doubt, the subject matter described herein is not limited by such examples. In addition, any aspect or design described herein as "exemplary" is not necessarily to be construed as preferred or advantageous over other aspects or designs, nor is it meant to preclude equivalent structures and techniques known to those of ordinary skill in the art. Furthermore, to the extent that the terms "includes," "has," "contains," and other similar words are used in either the detailed description or the claims, such terms are intended to be inclusive—in a manner similar to the term "comprising" as an open transition word—without precluding any additional or other elements.

Figure 1:
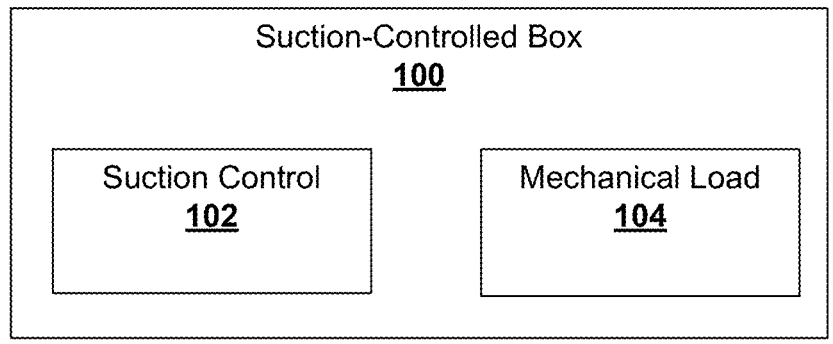
FIG. 1 illustrates a schematic block diagram of an exemplary suction-control box.

Referring now to FIG. 1, illustrated is a schematic system block diagram of an exemplary apparatus or device. In an embodiment, the device can be a suction-control box 100. The suction control box 100 can include two major components and/or parts, including a suction control part 102 and a mechanical load part 104. The suction control box 100 can be referred to as an integrated Humidity and Osmotic Suction-Controlled Box or a Hosmo Box.

The suction-controlled box 100 can test or measure important properties of a single soil sample. These important properties can include shear strength, stress-dependent soil-water characteristic curve, consolidation behavior, volume change (including swelling and shrinkage), and the like. The important properties can include any properties important to the study of soil behaviors.

The suction-controlled box 100 can operate under a wide range of suctions. For example, the suction-controlled box 100 can be operational to test or measure properties of a single soil sample for a full range of suctions (e.g. from 0 to 1,000 MPa). To ensure performance at different suctions, the suction-controlled box 100 can include a suction control part 102.

Figure 2:
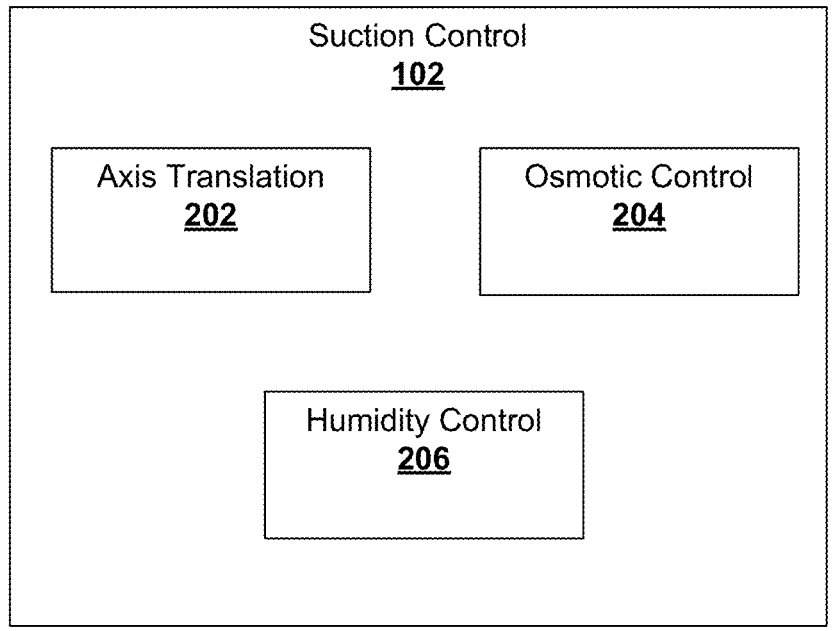
FIG. 2 illustrates a schematic block diagram of an exemplary suction control part of a suction-control box.

The suction control part 102 is schematically illustrated in FIG. 2. The suction control part 102 can include an axis translation component 202, an osmotic control component 204 and a humidity control component 206 that can each employ different techniques under different suction ranges throughout the full range of suctions (e.g. from 0 to 1,000 MPa). The axis control component 102 can employ an axis control technique at low suctions (e.g. less than about 500 kPa). The osmotic control component 204 can employ an osmotic control technique at medium suctions (e.g., from about 500 kPa to about 10 MPa). The humidity control component 206 can employ a humidity control technique at high suctions (e.g., greater than about 10 MPa). By combining the axis control component 202, the osmotic control component 204 and the humidity control component 206 in a single suction-controlled box 100, a full range if suctions (e.g. from 0 to 1,000 MPa) can be applied.

In many cases, soil is unsaturated in the natural state, such that pores are filled not only with a liquid (e.g., water), but also with gas (e.g., air). The co-existence of these two phases can lead to soil suction. It is generally recognized that soil suction controls both mechanical and hydraulic behaviors of unsaturated soils.

Soil suction generally refers to the potential of soil water, and can be calculated in terms of the partial vapor pressure of the soil water. In terms of thermodynamics, total soil suction can be defined in terms of the free energy of the soil water or the relative vapor pressure (relative humidity) of the soil water. According to Kelvin's equation, the relationship between total suction and the relative humidity can be described by Equation 1, $$\Psi = -\frac{RT}{v_{wo}\overline{\omega}_v}\ln\left(\frac{u_v}{u_{v0}}\right) = -\frac{RT}{v_{wo}\overline{\omega}_v}\ln(RH) \qquad \text{Equation (1)}$$

where $\Psi$ is the total suction (kPa); R is the universal (molar) gas constant (8.31432 J/(mol K)); T is the absolute temperature; $v_{wo}$ is the specific volume of water; $\overline{\omega}_v$ is the molecular mass of water vapor (18.016 kg/kmol), $u_v$ is the partial vapor pressure of pore-water pressure (kPa) and $u_{v0}$ is the saturation vapor pressure of water vapor over a flat surface of pure water at the same temperature (kPa); RH is relative humidity ($u_v/u_{v0}$).

Total suction, in other words, is the free energy of the soil water. In suction terms, it is the equivalent of the suction derived from the measurement of the partial pressure of the water vapor in equilibrium with the soil-water, relative to the partial pressure of the water vapor in equilibrium with free pure water. Total suction can be calculated based on matric suction (pore-air pressure ($u_a$)–pore water pressure ($u_w$)) and osmotic suction ($\pi$), so that:

$$\Psi = (u_a - u_w) + \pi \qquad \text{Equation (2)}$$

Matric suction, or the capillary component of free energy, represents the liquid tension generated through the interaction of soil water and the soil matrix and is defined as the pressure difference between the soil water and the pore gas. In terms of thermodynamics, it is the equivalent suction derived from the measurement of the partial pressure of the water vapor in equilibrium with the soil-water, relative to the partial pressure of the water vapor in equilibrium with a solution identical in composition with the soil water. Osmotic suction, or the solute component of free energy, is linked to the water solute potential. In suction terms, it is the equivalent suction level derived from the measurement of the partial pressure of the water vapor in equilibrium with a solution identical in composition with the soil-water, relative to the partial pressure of the water vapor in equilibrium with free pure water. Both the matric suction and the osmotic suction can be due to differences in relative humidity of the soil vapor.

It is important to control or measure suction in an unsaturated soil specimen. Generally, total suction can be controlled using the humidity control technique. Matric suction can be controlled by using the axis-translation technique. Osmotic suction can be controlled by using solutions with different solute concentrations, separated by a semi-permeable membrane.

Figure 3:
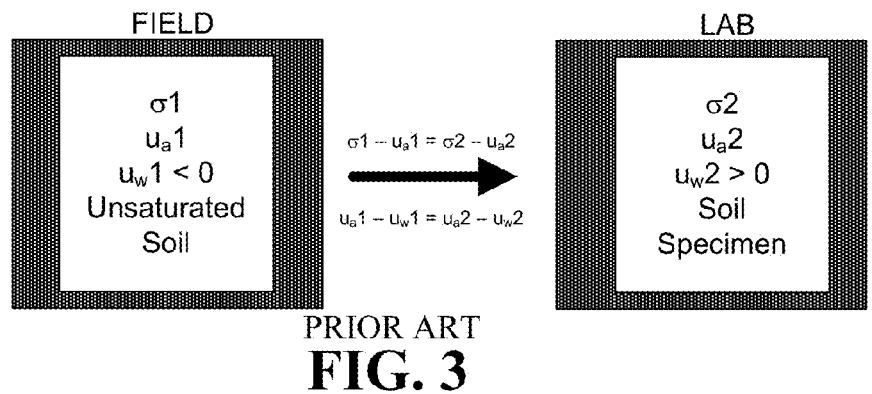
FIG. 3 is a schematic diagram illustrating the principle of axis translation.

For a low suction range (e.g., less than about 500 kPa), the axis translation component 202 can employ an axis translation technique to control unsaturated soil suction. A schematic diagram illustrating the principals of axis translation is shown in FIG. 3. With the axis translation technique, the pore air pressure ($u_a$) can be elevated to increase the pore water pressure ($u_w$) to be positive, preventing cavitations in water drainage systems. The total stress ($\sigma$) is increased with the air pressure by the same amount to maintain net stress ($\sigma-u_a$) unchanged. In this way, net stress, ($\sigma-u_a$), remains unchanged before and after the elevation of the pore air pressure ($\Delta u_a$). Similarly, matric suction ($u_a-u_w$) also remains unchanged since the elevation of pore air pressure ($\Delta u_a$) is the same as the increase in pore water pressure ($\Delta u_w$).

Axis translation is accomplished by separating the pore air in a soil specimen from the water phase of a pore water pressure measuring system normally located underneath the soil specimen by using a ceramic disk with a high air entry value. When saturated, this disk allows water passage, but prevents flow of free air to the pore water pressure measuring system when the applied matric suction does not exceed the air entry value of the porous disk. For example, the air entry value can be as high as 500 kPa for sintered ceramics or 1500 kPa for special cellulose membranes.

In the axis translation technique, both pore water pressure and pore air pressure are controlled and measured independently. One limitation of the axis translation technique pertains to the maximum value of suction that can be applied. It is limited by the maximum allowable cell pressure and the air entry value of the porous material. Hence, this technique generally is used for controlling suction on the order of hundreds of kilopascals (kPa).

Figure 4:
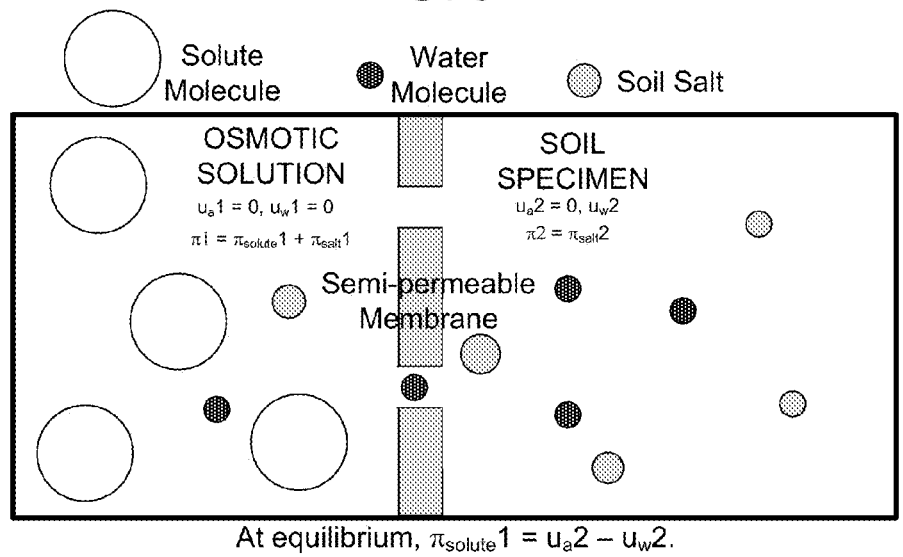
FIG. 4 is a schematic diagram illustrating the osmotic technique.

For a medium suction range (e.g., from about 500 kPa to about 10 MPa), the suction control component 204 can employ an osmotic control technique to measure or control unsaturated soil suction. A schematic diagram illustrating the principals the osmotic control technique is shown in FIG. 4. The phenomenon of osmosis is observed whenever a solvent and a solution are separated by a semi-permeable membrane, which only allows diffusion of solvent molecules. In this case, the solvent molecules are water molecules.

In the osmotic technique, the specimen and the osmotic solution are separated by a semi-permeable membrane. For example, suction control in a soil specimen can be based on a cellulotic semi-permeable membrane. Beneath the membrane, a solution is circulated. The membrane is permeable to water and ions in the soil, but impermeable to large solute molecules and soil particles. This results in a difference in solute concentration between the specimen and the solution, leading to a difference in osmotic potential across the semi-permeable membrane. The water energy on both sides of the membrane can prove that the matric suction in a soil specimen is equal to the osmotic suction (osmotic potential) of the solution in equilibrium. When the osmotic suction of the solution is greater than the matric suction of the specimen, water is drawn from the soil into the solution, increasing the suction in the specimen to achieve equilibrium.

At equilibrium, the component of osmotic suction related to soil salts is the same on both sides of the membrane, and the component of osmotic suction related to the solute is zero in the soil. The difference of osmotic suction related to the solute is zero in the soil. Then the difference of osmotic suction on both sides of the membrane is equal to the component of osmotic suction on both sides of the membrane is equal to the component of osmotic suction related to the solute in the solution. The pore air pressure ($u_a$) in the soil is at atmospheric pressure, similar to the natural condition in the field.

When water exchanged through the membrane is in equilibrium, the energy potential in soil-water is equal to that in solution-water. In other words, the total suction in the soil is equal to that in the solution. Therefore, the difference of osmotic suction is equal to the difference of matric suction on both sides of the membrane. Since the matric suction in the solution is zero, the matric suction ($u_a^2-u_w^2$) in the soil is equal to the difference in osmotic suction on both sides of the membrane (or equal to the component of osmotic suction related to the solute).

The osmotic technique can be based on a polyethylene glycol (PEG) solution or its equivalent to create suction for soil testing. Polyethylene glycol is the most commonly used solute because of its safety and simplicity. The value of osmotic suction depends on the concentration of the solution, such that the higher the concentration, the higher the osmotic suction. The maximum value of suction is limited only by the quality of a semi-permeable membrane and maximum osmotic potential (or concentration) of the solution. The maximum value of osmotic suction for a polyethylene glycol solution can be above about 10 MPa.

Figure 5:
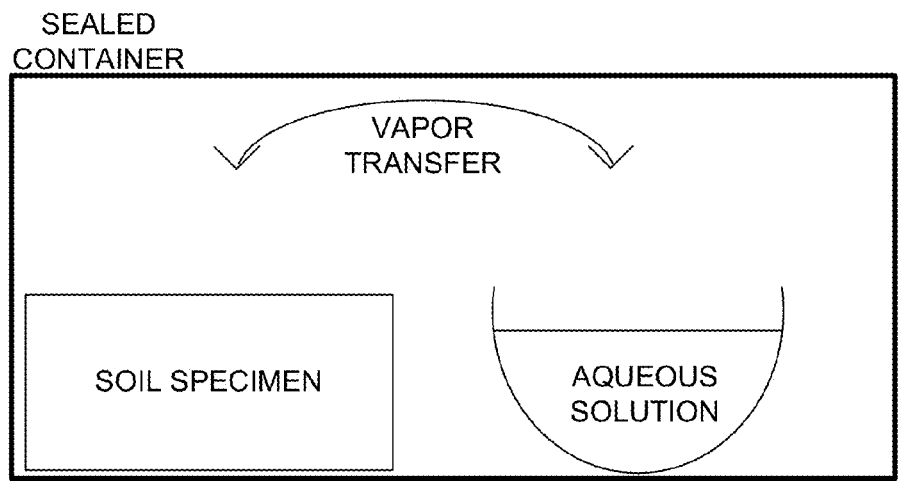
FIG. 5 is a schematic diagram illustrating the principle of humidity control with solutions.

For a high suction range (e.g. above about 10 MPa), the humidity control component 206 can employ a humidity control technique (or vapor equilibrium technique). Different saturated salt solutions can be chosen to provide different relative humidities for controlling various desirable total suctions. A schematic diagram illustrating the principals of humidity control is shown in FIG. 5. Based on the thermodynamic definition of Equation 1, total suction can be imposed on an unsaturated soil solution by controlling the relative humidity in the pores of the soil. Humidity can be controlled by using aqueous solutions or by mixing vapor-saturated gas with dry gas via a feedback system.

With the humidity control technique, a soil specimen can be placed in a closed thermodynamic environment assessing by an aqueous solution of a given chemical compound. Depending on the physio-chemical properties of the compound, a given relative humidity can be imposed within the sealed environment. Water exchanges occur by vapor transfer between the solution and the specimen until vapor equilibrium is achieved. The solution can be the same product at various concentrations, like unsaturated solutions, such as sulfuric acid or sodium chloride, or various saturated saline solutions. Saturated saline solutions have the practical advantage over unsaturated solutions of being able to liberate or adsorb relative large quantities of water without significantly affecting the equilibrium relative humidity.

By combining the axis translation component 202, the osmotic control component 204 and the humidity control component 206, the suction control part 102 of the suction-controlled box 100 can achieve a full suction range from 0-1,000 MPa.

Figure 6:
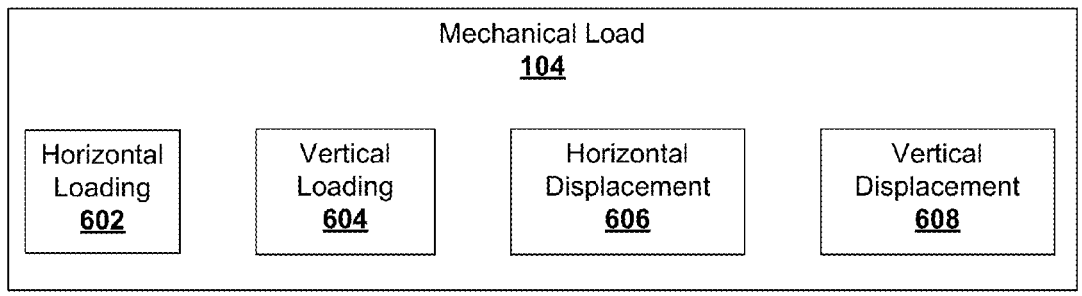
FIG. 6 illustrates a schematic block diagram of an exemplary mechanical loading part of a suction-controlled box.

The suction-controlled box 100 can also operate under a wide range of mechanical loading conditions. To enable different loading conditions, the suction-controlled box 100 can include a mechanical loading part 104. The mechanical loading part 104 is schematically illustrated in FIG. 6. The mechanical loading part 104 can include a horizontal loading component 602, a vertical loading component 604 and a horizontal displacement component 606 and a vertical displacement component 608. This can enable different mechanical loading conditions. One or more of components 602, 604, 606 and 608 can facilitate the measurement of properties, such as stress-dependent soil-water characteristic curve, shear strength, swelling, and consolidation. With the suction control part 102 and the mechanical loading part 104, the suction-controlled box can be operational for a variety of loading conditions and a wide range of suctions.

Figure 7:
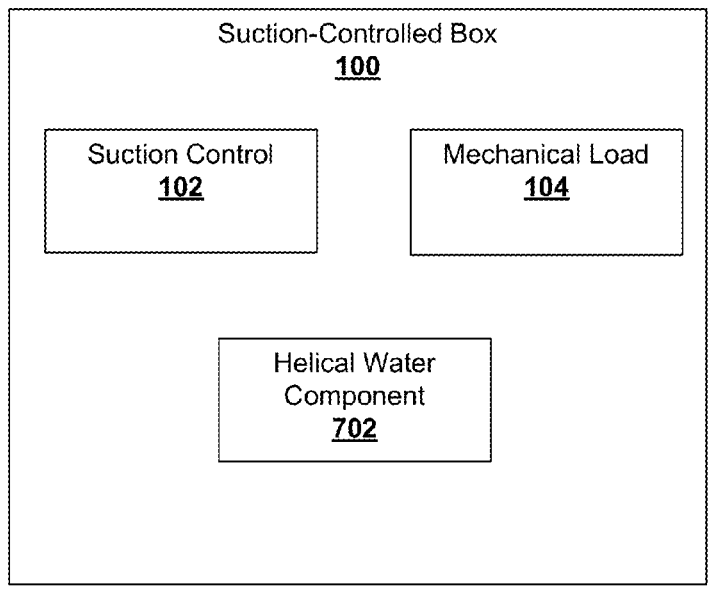
FIG. 7 illustrates a schematic block diagram of another exemplary suction-controlled box.

Illustrated in FIG. 7 is a schematic system block diagram of another embodiment of the suction-controlled box 100. The suction-controlled box 100 can include the suction control component 102 and the mechanical loading component 104 as described above. The suction-controlled box 100 can also include a helical water component 702.

During operation of the suction-controlled box 100, air diffusion can take place. Although air is diffused, diffused undissolved air bubbles can accumulate in the suction-controlled box 100. The helical water component 702 can flush away the accumulated air bubbles. The helical water component 702 can be a compartment. Additionally or alternatively, the helical water component 702 can be a pedestal.

Figure 8:
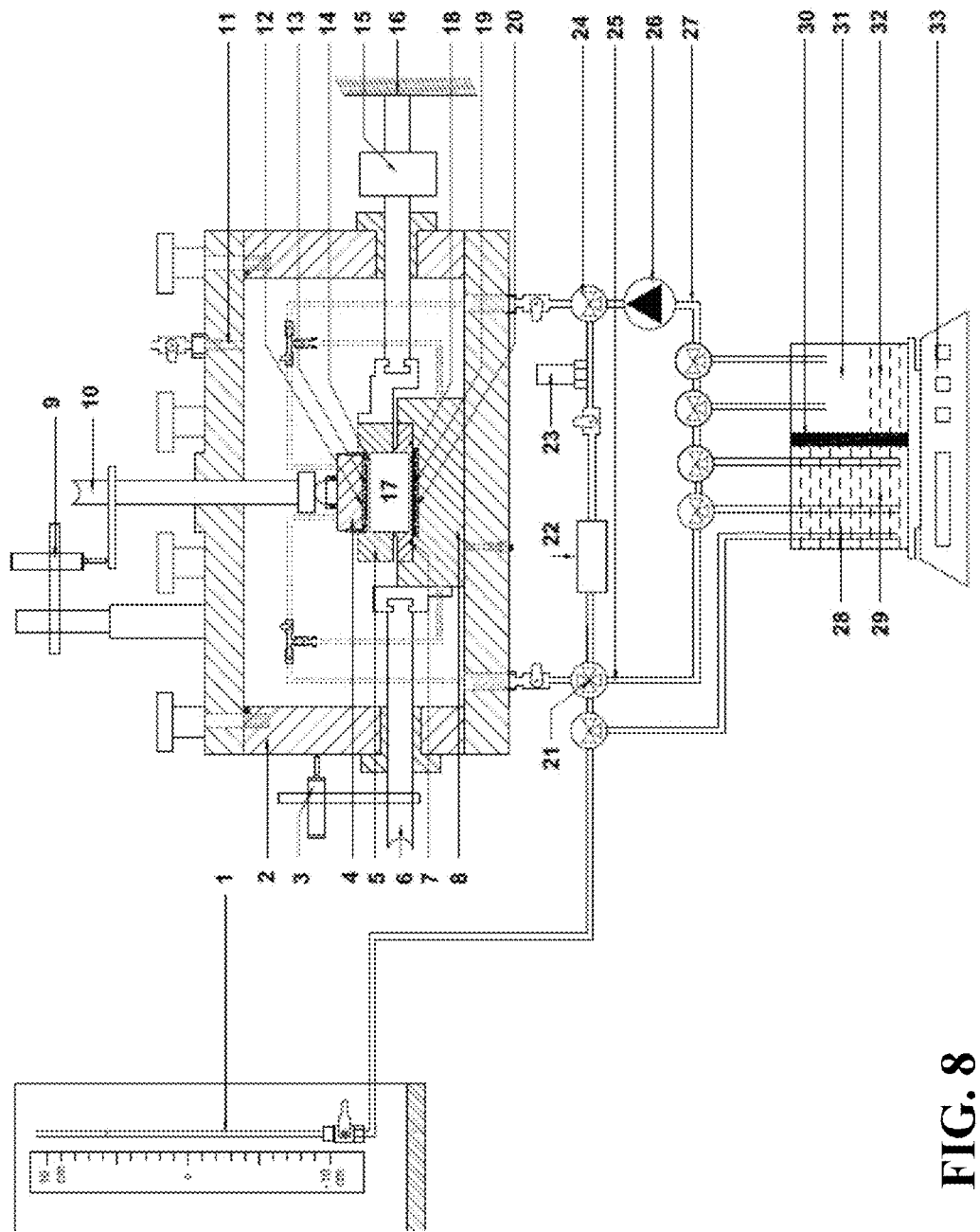
FIG. 8 illustrates a schematic diagram of a layout of an exemplary suction-controlled box.

Referring now to FIG. 8, illustrated us a schematic diagram of the layout of an example suction-controlled box. The suction-controlled box can include a burette 1, an air chamber 2, a horizontal Linear Variable Displacement Transformer 3, a loading cap 4, an upper box 5, a horizontal loading ram 6, a middle box 7, a lower box 8, a vertical Linear Variable Displacement Transformer 9, a vertical loading ram 10, an air valve for controlling pressurized air 11, a first helical water compartment 12, a first sieve 13, a first semi-permeable membrane or porous stone 14, a load cell 15, a reaction support 16, a soil specimen 17, a second semi-permeable membrane or high entry value ceramic disc 18, a second sieve 19, a second helical water compartment 20, a four way valve 21, a flushing system and diffused air volume indicator 22, a pore water pressure transducer 23, a three way valve 24, an inlet of polyethylene glycol solution/humidified air 25, a peristaltic pump 26, an outlet of polyethylene glycol solution/humidified air 27, a first compartment of a beaker 28, a polyethylene glycol solution 29, a central divider 30, a second compartment of the beaker 31, a saturated salt solution 32, an electronic balance 33, a chamber cap 34, a chamber body 35, a chamber base 36, a reaction rod 37, a cap screw 38, a rubber o-ring 39, an air outlet 40, and a case of loading cap 41.

The suction-controlled box can include three suction controls. The air chamber 2 and air valve for controlling pressurized air 11 can be utilized to employ the axis translation technique that can be applied for suctions less than about 500 kPa. The first compartment of the beaker 28 filled with the polyethylene glycol solution 29 can be utilized to employ the osmotic control technique that can be applied for suctions between about 500 kPa and about 10 MPa. The second component of the beaker 31 filled with saturated salt solution 32 can be utilized to employ the humidity control technique for suctions above about 10 MPa.

For low suctions (e.g., below 500 kPa), the axis translation technique can be employed. To control an air pressure ($u_a$), a high pressurized air pressure can be applied to the air chamber 2 via the air valve 11. To prevent the pressurized air from entering the second helical water compartment 20 under the specimen, a high air-entry value disk 18 is installed at the bottom of the soil specimen 17. The water pressure ($u_w$) inside the second helical water compartment 20 can be measured by using a pore water pressure transducer 23 via a three-way valve 24. The difference between $u_a$ and measured $u_x$ is called matric suction. The axis translation technique is limited for suctions below about 500 kPa.

Based on the principal of osmosis, the osmotic control technique can be applied for suctions between about 500 kPa and about 10 MPa. For the osmotic control technique, various concentrations of the polyethylene glycol solution 29 can be used. To achieve the soil suction between about 500 kPa and about 10 MPa, a calibrated concentration of the polyethylene glycol solution 29 can be stored in the first compartment of the beaker 28. The polyethylene glycol solution 29 is pumped by the peristaltic pump 26 to reach the first semi-permeable membrane 14 located at the top of the soil specimen 17 and is also pumped to the second semi-permeable membrane 18 located at the bottom of the soil specimen 17. The two semi-permeable 14, 18 membranes are permeable to water and ions in the soil specimen 17, but impermeable to large solute molecules and soil particles. This results in a difference in solute concentration between the soil specimen 17 and the polyethylene glycol solution 29, which leads to a difference in osmotic potential across the two membranes. Osmotic potential of the polyethylene glycol solution 29 causes drainage of the soil specimen 17, and is finally balanced by the negative pore water in the soil specimen 17. At equilibrium, soil suction in the soil specimen 17 is equal to the osmotic suction (osmotic potential) of the polyethylene glycol solution 29. When the osmotic suction of the polyethylene glycol solution 29 is greater than the suction in the soil specimen 17, water is drawn from the soil specimen 17 and regulated by a four way valve 21 and measured by a burette 1. Since the air pressure around a soil specimen 17 remains atmospheric11, the field stress path is better simulated using the osmotic technique.

At suctions above about 10 MPa, the osmotic technique is not an ideal, so the humidity control technique is employed for these high suctions. According Equation 1, total suction can be controlled by relative humidity in soil pores, and the humidity control technique controls this relative humidity. A saturated salt solution 32 can be stored inside the second compartment of the beaker 31. The stored salt solution 32 can create a relative humidity of moist air, which can then be pumped to circulate to the entire system by a peristaltic pump 26 to reach and equalize with the soil specimen 17 in the upper box 5 and the middle box 7. The moist air then returns to the second compartment of the beaker 31. At a given suction, any excessive volume of water vapor flowing out of or in to the soil specimen will be collected or provided by the second compartment of the beaker 31 and the amount can be measured by an electronic balance 33.

By combining the axis translation technique, the osmosis control technique, and the humidity control technique, the suction-controlled box can achieve a full range of suctions from 0 to 1,000 MPa. The suction-controlled box can also achieve various mechanical loading and hydraulic conditions independently or simultaneously.

The suction-controlled box includes a mechanical loading part that includes a vertical loading system and a horizontal loading system. The mechanical loading part also includes a vertical displacement measuring device.

In the suction-controlled box, a vertical load can be applied by the vertical loading ram 10. A vertical displacement of the soil specimen 17 can be measured by a linear variable displacement transformer 9. If a shear force is needed, a horizontal force can be applied to the lower half of the soil specimen 17 by the horizontal loading ram 6 and the force can be measured by a load cell 15. The horizontal movement of the loading system 6 can be measured by a horizontal linear variable displacement transformer 3.

During operation of the suction-controlled box, air diffusion takes place. Diffused but undissolved air can accumulate underneath the lower second semi-permeable membrane 18. This air can be flushed away via the second helical water compartment 20.

Figure 9:
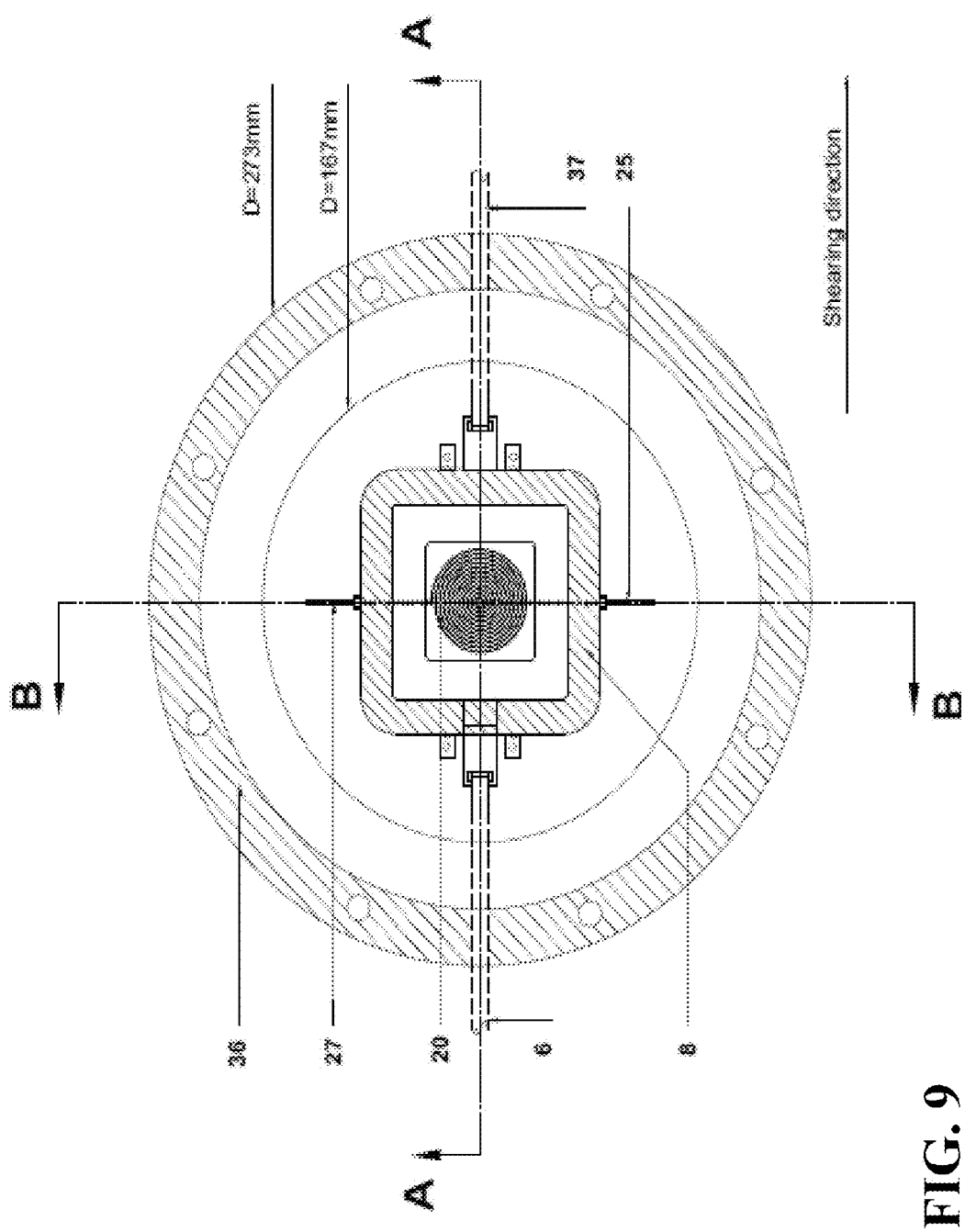
FIG. 9 illustrates a schematic plan view of an exemplary suction-controlled box.
Figure 10:
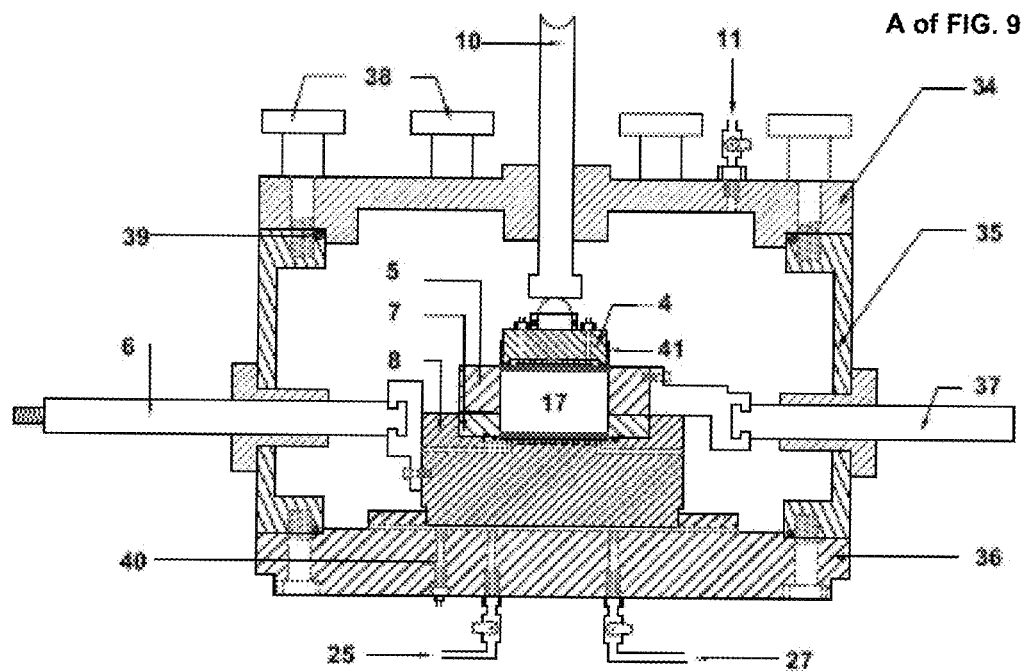
FIG. 10 illustrates a schematic plan view of section A of the exemplary suction-controlled box of FIG. 9.

Referring now to FIG. 9, illustrated is a plan view of the suction-controlled box as shown in FIG. 10. For ease of illustration, section A in FIG. 9 is expanded in FIG. 10. Similarly, section B in FIG. 9 is expanded in FIG. 11.

Figure 11:
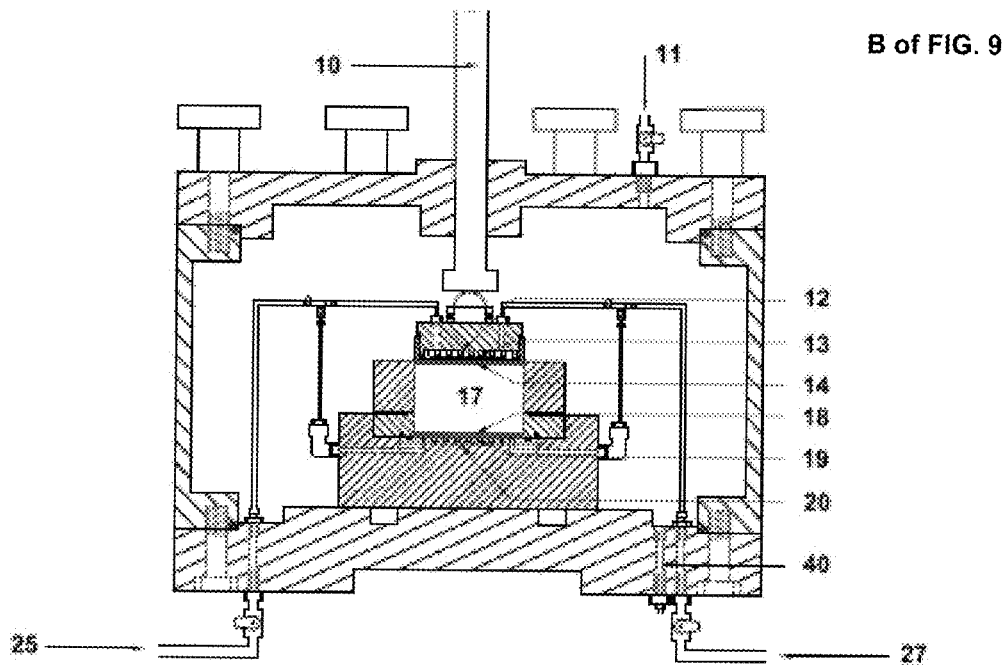
FIG. 11 illustrates a plan view of section B of the exemplary suction-controlled box of FIG. 9.

Illustrated in FIG. 9 is the horizontal loading ram 6, the lower box 8, the second helical water compartment 20, the inlet of polyethylene glycol solution/humidified air 25, the outlet of polyethylene glycol solution/humidified air 27, a chamber base 36, and a reaction rod 37. Element A as illustrated in FIG. 8 and expanded in FIG. 10 includes the loading cap 4, the upper box 5, the horizontal loading ram 6, the middle box 7, the lower box 8, the vertical loading ram 10, the air valve for controlling pressurized air 11, the soil specimen 17, the inlet of polyethylene glycol solution/humidified air 25, the outlet of polyethylene glycol solution/humidified air 27, a chamber cap 34, a chamber body 35, the chamber base 36, the reaction rod 37, a cap screw 38, a rubber O-ring 39, an air outlet 40, and a case of loading cap 41. Element B as illustrated in FIG. 8 and expanded in FIG. 11 includes the vertical loading ram 10, the air valve for controlling pressurized air 11, the first helical water compartment 12, the first sieve 13, the first semi-permeable membrane or porous stone 14, the soil specimen 17, the second semi-permeable membrane or high entry value ceramic disc 18, the second sieve 19, the second helical water compartment 20, the inlet of polyethylene glycol solution/humidified air 25, the outlet of polyethylene glycol solution/humidified air 27, and an air outlet 40. Functionality of the suction-controlled box as illustrated in FIGS. 9, 10 and 11 can be the same as the functionality of the suction-controlled box as illustrated in FIG. 8.

Figure 12:
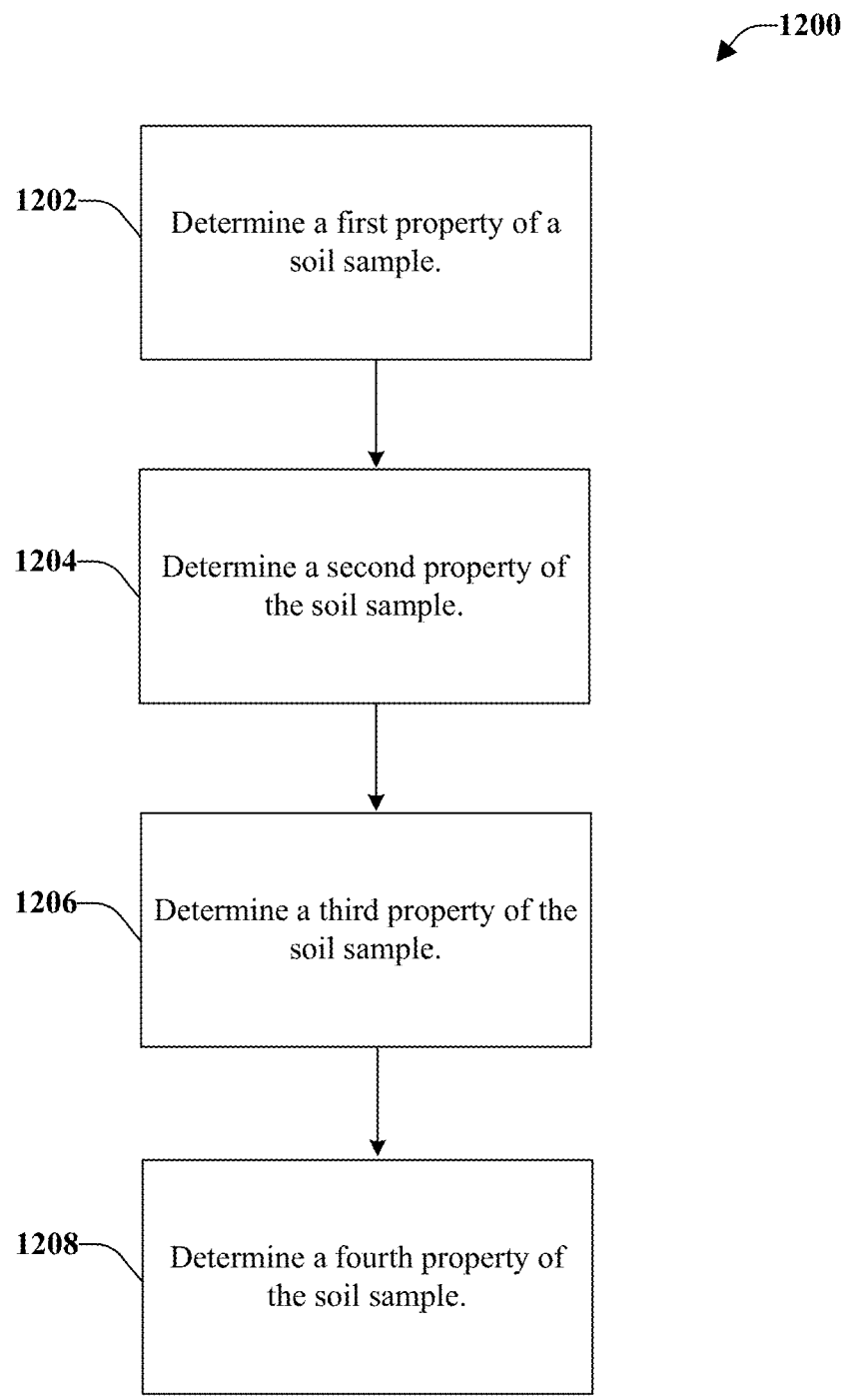
FIG. 12 illustrates a schematic process flow diagram of a method for measuring and determining various properties of a single soil specimen.
Figure 13:
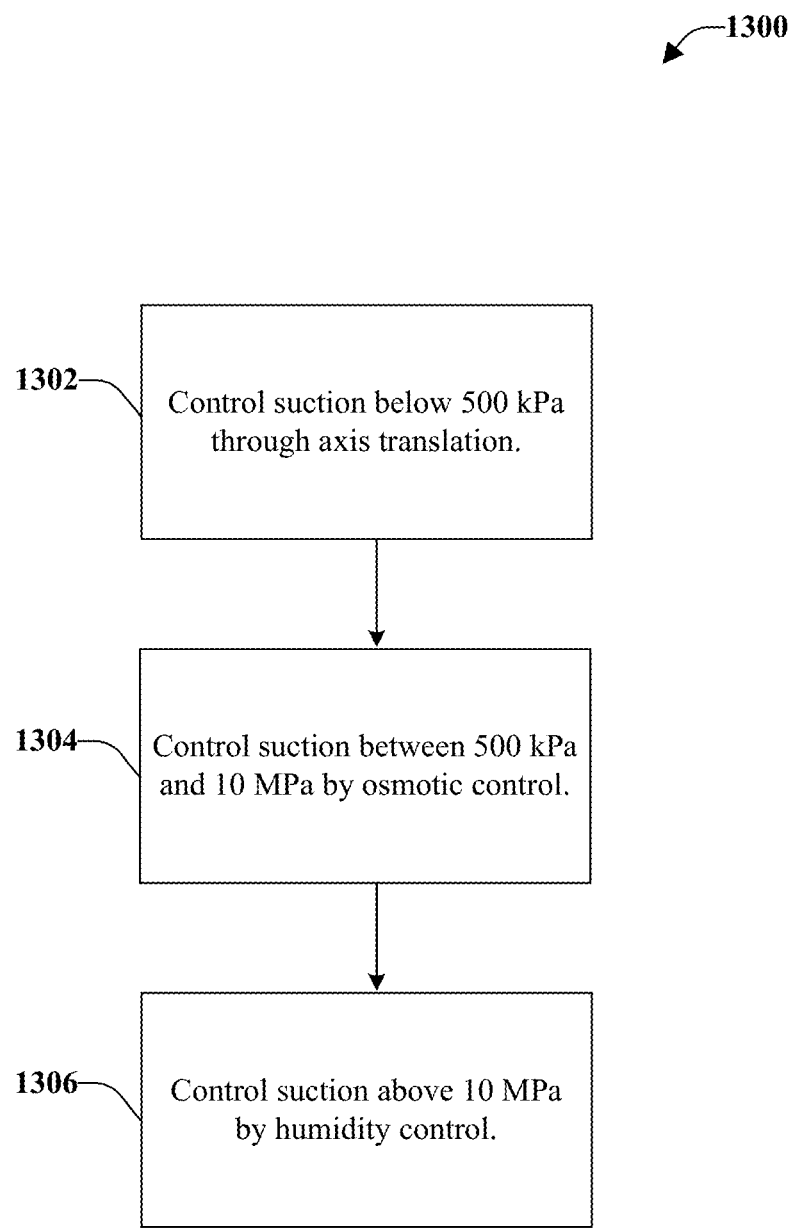
FIG. 13 illustrates a schematic process flow diagram of different suction control methods adopted in a suction-controlled box for a suction range from 0 to 1,000 MPa.
Figure 14:
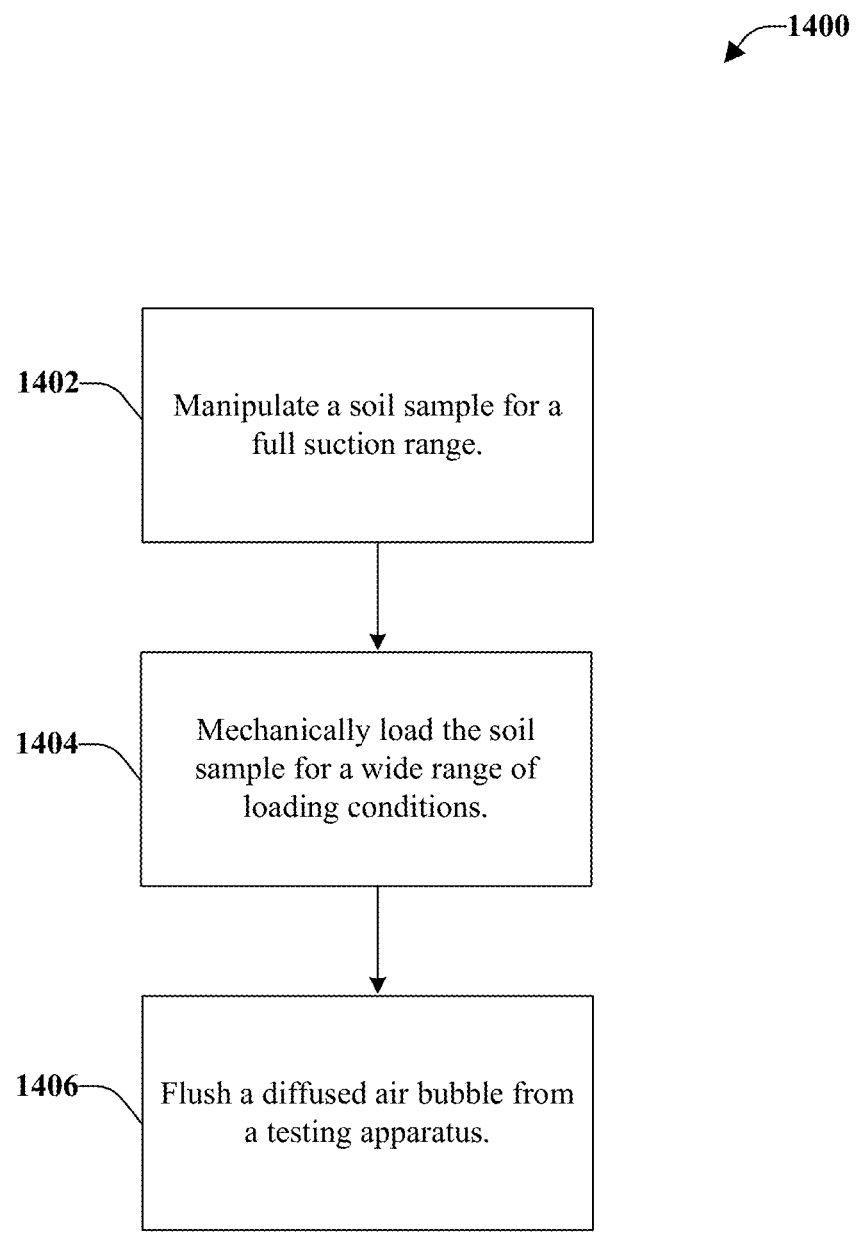
FIG. 14 illustrates a schematic process flow diagram of a method for measuring and determining various mechanical and hydraulic behaviors and properties from a single soil specimen.

FIGS. 12-14 illustrate methods or algorithms that can be utilized, for example, in connection with the suction-controlled device illustrated in FIGS. 8-11 above. For simplicity of explanation, the methods and algorithms are depicted and described as a series of acts. It is to be understood and appreciated that the various embodiments are not limited by the acts illustrated and/or by the order of acts. For example, acts can occur in various orders and/or concurrently, and with other acts not presented or described herein. Furthermore, not all illustrated acts can be required to implement the methods or algorithms as described herein. In addition, those skilled in the art will understand and appreciate that the methods or algorithms could alternatively be represented as a series of interrelated states via a state diagram or events.

Referring now to FIG. 12, illustrated is a schematic process flow diagram of a method 1200 for testing, measuring or determining various properties of a single soil sample. The soil sample can be an unsaturated soil sample. The soil sample can also be a saturated soil sample. The same soil sample can be used throughout method 1200.

The method begins at element 1202, where a first property of a soil sample can be determined. At element 1204, a second property of the same soil sample can be determined on the same apparatus. The apparatus can be, for example, the suction-controlled box as shown in FIG. 8-11. At element 1206, a third property of the same soil sample can be determined on the same apparatus. At element 1206, a fourth property of the same soil sample can be determined on the same apparatus.

The first property, the second property, the third property and the fourth property can include important geotechnical and hydraulic properties, such as shear strength, stress-dependant soil-watch characteristic curve and indirect permeability functions, consolidation behavior (including settlement), volume (including swelling and shrinkage), water content, and the like. These properties can be any mechanical or hydraulic properties of the soil sample. The apparatus can be a suction-controlled box that can provide a single integrated system that can test these mechanical and hydraulic behaviors and properties from a single soil specimen while controlling a full range of suctions (e.g., from 0 to 1,000 MPa).

Referring now to FIG. 13, illustrated is a schematic process flow diagram of a method 1300 for manipulating a soil sample for a suction range from 0 to 1,000 MPa. The soil sample can be an unsaturated soil sample. The soil sample can also be a saturated soil sample. The same soil sample can be used throughout method 1300. The full suction range can be accomplished by a suction-controlled box that can provide an integrated system that can test mechanical and hydraulic behaviors and properties from the single soil specimen for a full range of suctions.

At element 1302, the apparatus can control the suctions below about 500 kPa using an axis translation technique. With the axis translation technique, soil pore air pressure ($u_a$) can be elevated to increase the soil pore water pressure ($u_w$) to be positive, preventing cavitations in water drainage systems. The total stress ($\sigma$) is increased with the air pressure by the same amount to maintain net stress ($\sigma$-$u_a$) unchanged. In this way, net stress, ($\sigma$-$u_a$), remains unchanged before and after the elevation of the pore air pressure ($\Delta u_a$). Similarly, matric suction ($u_a-u_w$) also remains unchanged since the elevation of pore air pressure ($\Delta u_a$) is the same as the increase in pore water pressure ($\Delta u_w$). Axis translation is accomplished by separating the pore air in a soil specimen from the water phase of a pore water pressure measuring system normally located underneath the soil specimen by using a ceramic disk with a high air entry value. When saturated, this disk allows water passage, but prevents flow of free air to the pore water pressure measuring system when the applied matric suction does not exceed the air entry value of the porous disk. The axis translation technique is limited by the maximum value of cell pressure and the air entry value of the porous material (on the order of hundreds of kPa).

At element 1304, the apparatus can control the suction between about 500 kPa and about 10 MPa using an osmotic control technique. In the osmotic technique, the specimen and the osmotic solution are separated by a semi-permeable membrane. For example, suction control in a soil specimen can be based on a cellulotic semi-permeable membrane. Beneath the membrane, a solution is circulated. The membrane is permeable to water and ions in the soil, but impermeable to large solute molecules and soil particles. This results in a difference in solute concentration between the specimen and the solution, leading to a difference in osmotic potential across the membrane. The difference in osmotic potential of the solution and the soil water leads to drainage (in or out) of soil specimen and the potential is finally balanced by the negative pore water pressure in the specimen The water energy on both sides of the membrane can prove that the matric suction in a soil specimen is equal to the osmotic suction (osmotic potential) if the solution in equilibrium. When the osmotic suction of the solution is greater than the matric suction of the specimen, water is drawn from the soil into the solution, increasing the suction in the specimen to achieve equilibrium.

At equilibrium, the component of osmotic suction related to soil salts is the same on both sides of the membrane, and the component of osmotic suction related to the solute is zero in the soil. The difference of osmotic suction related to the solute is zero in the soil. Then the difference of osmotic suction on both sides of the membrane is equal to the component of osmotic suction on both sides of the membrane is equal to the component of osmotic suction related to the solute in the solution. The pore air pressure ($u_a$) in the soil is at atmospheric pressure, similar to the natural condition in the field.

When water exchange through the membrane is in equilibrium, the energy potential in soil-water is equal to that in solution-water. In other words, the total suction in the soil is equal to that in the solution. Therefore, the difference of osmotic suction is equal to the difference of matric suction on both sides of the membrane. Since the matric suction in the solution is zero, the matric suction ($u_a^2-u_w^2$) in the soil is equal to the difference in osmotic suction on both sides of the membrane (or equal to the component of osmotic suction related to the solute).

The osmotic technique can be based on a polyethylene glycol (PEG) solution or its equivalent to create suction for soil testing. Polyethylene glycol is the most commonly used solute because of its safety and simplicity. The value of osmotic suction depends on the concentration of the solution, such that the higher the concentration, the higher the osmotic suction. The maximum value of suction is limited by the maximum osmotic suction potential (i.e., concentration) of the solution (above about 10 MPa) and the quality of a semi-permeable membrane.

At element 1306, the apparatus can control suctions above about 10 MPa using a humidity control technique. With the humidity control technique, a soil specimen can be placed in a closed thermodynamic environment containing a saturated aqueous solution of a given chemical compound. Depending on the physio-chemical properties of the compound, a given relative humidity can be imposed within the sealed environment. Water exchanges occur by vapor transfer between the solution and the specimen until vapor equilibrium is achieved.

Referring now to FIG. 14, illustrated is a schematic process flow diagram of a method 1400 for measuring or testing various mechanical and hydraulic behaviors and properties of a single soil sample. The soil sample can be an unsaturated soil sample. The soil sample can also be a saturated soil sample. The same soil sample can be used throughout method 1400. The various mechanical and hydraulic behaviors and properties can include important geotechnical and hydraulic properties, such as shear strength, stress-dependant soil-watch characteristic curve and indirect permeability functions, consolidation behavior (including settlement), volume (including swelling and shrinkage), water content, and the like.

At element 1402, a soil sample is manipulated for a suction range from 0 to 1,000 MPa. For a suction range from 0-about 500 kPa, an axis translation technique is used. For a suction range of about 500 kPa-10 MPa, an osmotic control technique is used. For a suction range from about 10 MPa-about 1,000 MPa, a humidity control technique is used. The combination of these techniques allows the soil sample to be manipulated for a suction range from 0 to 1,000 MPa.

At element 1404, the same soil sample is mechanically loaded under a wide range of mechanical loading conditions, including horizontal loading and vertical loading, and together with the measurements of horizontal and vertical displacements. The loading conditions can facilitate testing or measurement of properties, such as stress-dependent soil-water characteristic curve, shear strength, swelling, and consolidation.

At element 1406, a diffused air bubble is flushed away from the soil sample. During operation of an apparatus for various suction conditions and mechanical load conditions, air diffusion can take place. Although air is diffused, diffused undissolved air bubbles can accumulate near the soil sample. These accumulated air bubbles cam be flushed away by a specially designed portion of the apparatus (e.g., a pedestal or a compartment).

The above description of illustrated embodiments, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims.

What is claimed is:

1. A suction-controlled box, comprising:
   a suction control part that facilitates manipulation of a suction of a single soil specimen; and a mechanical loading part that facilitates measurement of a displacement for a loading of the single soil specimen, wherein the suction-controlled box is configured to determine at least four soil properties for the single soil specimen.

2. The suction-controlled box of claim 1, wherein the at least four soil properties include shear strength.

3. The suction-controlled box of claim 1, wherein the at least four soil properties include a stress-dependent soil-water characteristic curve.

4. The suction-controlled box of claim 1, wherein the at least four soil properties include a consolidation behavior.

5. The suction-controlled box of claim 1, wherein the at least four soil properties include a volume change.

6. The suction-controlled box of claim 1, wherein the suction-control part is operable for a range of suctions from 0 kPa to 1,000 MPa.

7. The suction-controlled box of claim 1, wherein the suction-control part comprises:

an axis translation unit operable to manipulate the suction of the single soil specimen for suctions less than about 500 kPa;

an osmotic control unit operable to manipulate the suction of the single soil specimen for suctions from about 500 kPa to about 10 MPa; and a relative humidity control unit operable to manipulate the suction of the single soil specimen for suctions greater than about 10 MPa.

8. The suction-controlled box of claim 1, wherein the mechanical loading part comprises:

a horizontal loading system configured to measure the displacement for the loading of the single soil specimen in a horizontal direction; and a vertical loading system configured to measure the displacement for the loading of the single soil specimen in a vertical direction.

9. The suction-controlled box of claim 1, wherein the single soil specimen is an unsaturated soil specimen.

10. A method, comprising:

manipulating a suction of a soil sample on a single device for a range of suctions between 0 and about 1,000 MPa, wherein the manipulating the suction comprises combining an axis control technique for suctions less than about 500 kPa, an osmosis technique for suctions between about 500 kPa and about 10 MPa, or a humidity control technique for suctions greater than about 10 MPa;

determining a first property for the soil sample on the single device;

determining a second property for the soil sample on the single device;

determining a third property for the soil sample on the single device; and determining a fourth property for the soil sample on the single device.

11. The method of claim 10, wherein the manipulating the suction of the soil sample comprises manipulating the suction of an unsaturated soil sample.

12. The method of claim 10, wherein at least one of the determining the first property, the determining the second property, the determining the third property, or the determining the fourth property comprises determining a shear strength for the soil sample.

13. The method of claim 10, wherein at least one of the determining the first property, the determining the second property, the determining the third property, or the determining the fourth property comprises determining a stress-dependent soil-water characteristic curve for the soil sample.

14. The method of claim 10, wherein the osmotic technique further comprises employing a solution with similar characteristics to polyethylene glycol and creating the suction between 500 kPa and 10 MPa.

15. The method of claim 10, wherein at least one of the determining the first property, the determining the second property, the determining the third property, or the determining the fourth property comprises determining a consolidation behavior for the soil sample.

16. The method of claim 10, wherein at least one of the determining the first property, the determining the second property, the determining the third property, or the determining the fourth property comprises determining a volume change for the soil sample.

17. The method of claim 10, further comprising loading the soil sample in a vertical direction and measuring displacement in the vertical direction.

18. The method of claim 10, further comprising loading the soil sample in a horizontal direction and measuring displacement in the horizontal direction.

19. The method of claim 10, further comprising flushing a diffused air bubble away from the single device.

20. A suction-controlled box, comprising:

means for manipulating a soil sample for a suction range from 0 to 1,000 MPa;

means for mechanically loading the soil sample; and means for flushing a diffused air bubble from the suction-controlled box.

* * * * *